US 9,280,685 B2

(12) United States Patent
Jackson (10) Patent No.: US 9,280,685 B2
(45) Date of Patent: Mar. 8, 2016

(54) SYSTEM AND METHOD FOR PORTABLE MEDICAL RECORDS

(76) Inventor: Johnnie R. Jackson, Fort Washington, MD (US)

(*) Notice: Subject to any disclaimer, the term of this patent is extended or adjusted under 35 U.S.C. 154(b) by 0 days.

(21) Appl. No.: 11/979,069

(22) Filed: Oct. 30, 2007

(65) Prior Publication Data
US 2008/0140572 A1   Jun. 12, 2008

Related U.S. Application Data

(60) Provisional application No. 60/873,562, filed on Dec. 8, 2006.

(51) Int. Cl.
*G06F 21/00* (2013.01)
*G06F 21/62* (2013.01)
*G06F 21/78* (2013.01)
*G06Q 50/24* (2012.01)
*G06F 19/00* (2011.01)

(52) U.S. Cl.
CPC .......... *G06F 21/6245* (2013.01); *G06F 19/323* (2013.01); *G06F 21/78* (2013.01); *G06Q 50/24* (2013.01); *G06F 19/322* (2013.01)

(58) Field of Classification Search
USPC .......................................................... 705/50
See application file for complete search history.

(56) References Cited

U.S. PATENT DOCUMENTS

| 5,388,433 | A | * | 2/1995 | Andersson | .......... E05B 73/0017 109/25 |
| 5,768,389 | A | * | 6/1998 | Ishii | ...................... H04L 9/0897 380/277 |
| 6,088,786 | A | * | 7/2000 | Feierbach et al. | ............ 712/200 |
| 6,914,694 | B1 | * | 7/2005 | Ichikawa | ........... H04N 1/00137 358/1.15 |
| 7,028,049 | B1 | | 4/2006 | Shelton | |

(Continued)

FOREIGN PATENT DOCUMENTS

| DE | 199 53 699 | 5/2001 |
| JP | 11-312201 | 11/1999 |

(Continued)

OTHER PUBLICATIONS

"Portable Health Profile (Individual)", website: http://www.desertmedicalessentials.com/product_info.php?cPath=23_90&products_id=396, 2 pages, printed from the Internet on Jul. 10, 2006.

(Continued)

*Primary Examiner* — Dante Ravetti
(74) *Attorney, Agent, or Firm* — Richard C. Litman (57) ABSTRACT

The system and method for portable medical records provides an electronic medical record that is stored in a key fob-sized portable device. A user can purchase the portable device and upload his/her medical record to the device over the Internet, after which the device is sent to the user. The user accesses the device for information in the portable electronic medical record and adds information when necessary. An encryption system controls health provider access to the information stored in the device. The ability to read, write or modify information can be made specific to a particular group of health care providers. Access to the portable electronic medical record can be limited to an individual patient and his/her designated authorized healthcare provider(s). Medical record information transfer is done via secure communication between a computer and the portable electronic device to assure compliance with applicable medical record privacy laws.

5 Claims, 8 Drawing Sheets

(56) References Cited

U.S. PATENT DOCUMENTS

| | | |
|---|---|---|
| 7,204,425 B2* | 4/2007 | Mosher et al. .............. 235/492 |
| 2001/0041991 A1 | 11/2001 | Segal et al. |
| 2002/0022972 A1 | 2/2002 | Costello |
| 2002/0046061 A1 | 4/2002 | Wright et al. |
| 2002/0065854 A1 | 5/2002 | Pressly |
| 2003/0036683 A1* | 2/2003 | Kehr .................... G06F 19/325 600/300 |
| 2003/0037065 A1 | 2/2003 | Svab |
| 2003/0069759 A1* | 4/2003 | Smith ............................. 705/3 |
| 2003/0088440 A1 | 5/2003 | Dunn |
| 2003/0114896 A1 | 6/2003 | Boute et al. |
| 2003/0154411 A1 | 8/2003 | Hovik |
| 2003/0158754 A1 | 8/2003 | Elkind |
| 2003/0173408 A1* | 9/2003 | Mosher ................. A61B 5/117 235/492 |
| 2004/0093155 A1* | 5/2004 | Simonds ................. H04L 67/12 701/532 |
| 2004/0103001 A1 | 5/2004 | Mazar et al. |
| 2004/0122719 A1* | 6/2004 | Sabol .................... G06F 19/324 705/7.13 |
| 2004/0172307 A1 | 9/2004 | Gruber |
| 2004/0199408 A1 | 10/2004 | Johnson |
| 2005/0021519 A1 | 1/2005 | Ghouri |
| 2005/0043827 A1* | 2/2005 | Schaeffer ............. G06F 19/323 700/72 |
| 2005/0052844 A1* | 3/2005 | McCollum et al. ........... 361/689 |
| 2005/0065813 A1 | 3/2005 | Mishelevich et al. |
| 2005/0075909 A1 | 4/2005 | Flagstad |
| 2005/0086082 A1 | 4/2005 | Braunstein et al. |
| 2005/0109841 A1* | 5/2005 | Ryan .................... G06F 13/385 235/380 |
| 2005/0165627 A1 | 7/2005 | Fotsch et al. |
| 2005/0209975 A1* | 9/2005 | So ......................... G06F 21/606 705/71 |
| 2005/0216313 A1 | 9/2005 | Claud et al. |
| 2005/0277872 A1 | 12/2005 | Colby, Jr. et al. |
| 2006/0010012 A1* | 1/2006 | Franzblau et al. ................ 705/2 |
| 2006/0020012 A1* | 1/2006 | Jones .................. C07D 231/12 514/407 |
| 2006/0064320 A1* | 3/2006 | Postrel .............................. 705/2 |
| 2006/0074718 A1 | 4/2006 | Fucci et al. |
| 2006/0106648 A1 | 5/2006 | Esham et al. |
| 2006/0208066 A1* | 9/2006 | Finn ..................... G06K 7/0004 235/380 |
| 2007/0143629 A1* | 6/2007 | Hardjono ............ H04L 63/0823 713/189 |
| 2007/0255698 A1* | 11/2007 | Kaminaga ......... G06F 17/30522 |
| 2008/0058664 A1* | 3/2008 | Mirro ................. A61N 1/37211 600/523 |

FOREIGN PATENT DOCUMENTS

| | | |
|---|---|---|
| JP | 2001-344347 | 12/2001 |
| JP | 2003-44478 | 2/2003 |

OTHER PUBLICATIONS

"REDmic Personal Health Information", website: http://www.redmedic.com/jsp/site/Portal.jsp?page_id=6, 2 pages, printed from the Internet on Jul. 10, 2006.

* cited by examiner

SYSTEM AND METHOD FOR PORTABLE MEDICAL RECORDS

CROSS-REFERENCE TO RELATED APPLICATION

This application claims the benefit of U.S. Provisional Patent Application Ser. No. 60/873,562, filed Dec. 8, 2006.

BACKGROUND OF THE INVENTION

1. Field of the Invention

The present invention relates to computerized systems and methods for maintaining medical records, and particularly to a system and method for portable medical records that permits a patient to carry an electronic version of the medical records upon his or her person while maintaining patient privacy.

2. Description of the Related Art

Very few people, if any, carry their medical records around with them. Many people have portions of their hardcopy and computer-based medical records scattered throughout different locations, such as their homes, offices, hospitals, and various health care providers' offices. Often, people simply do not know where their medical records are located.

In numerous instances, healthcare providers have erroneously convinced patients that the provider owns the medical record and not the patient. Therefore, many providers refuse to give the patient his/her medical record. It is critical that each person has a copy of every treatment episode that may be encountered by the person at any and all medical facilities so that all treatments are documented in order to provide healthcare providers with a comprehensive and accurate patient history. Moreover, these documents are critical because medical records or portions thereof frequently get lost.

In addition, these medical records are critical in cases of malpractice resulting in medical claims and lawsuits. In other words there exists a long felt need for a medical records "black box" that is conveniently updated with each medical episode and that can be examined in the event that something goes wrong to determine the root cause(s) of the problem.

The healthcare industry is the only industry in America where nearly 100% of the people must be a part of from months before birth, while they are living, and in many instances after they are dead.

There is a long felt need for a method, process, or system that has the capability to play a significant role in revolutionizing the healthcare industry by providing people with the capability to have their patient medical data readily accessible, and in an electronic media so that the data can be used to: 1) possibly save the patients life by providing the medical data to the healthcare professional in a complete, accurate, concise, cost-effective and timely manner for effective medical treatment of the patient regardless of location; 2) provide the patient's medical data for treatment purposes involving emergency situations, such as when traveling, loss of prescriptions for medications (especially necessary with patients with diabetes, epilepsy, cardiac patients, patients with special needs, and the like), dental records, eye glasses, etc.; and 3) drastically reduce medical triage costs in emergency situations where the patient is not seen at the facility where her/his medical records are being maintained. It is estimated that medical triage costs involved in vehicular accidents amount to over $300 per episode. Most of these costs could possibly be eliminated if the patient has a medical record in his/her possession at all times.

Moreover, there exists a long-felt need for a portable medical record that can be used by anyone interested in his/her healthcare and well-being, medical facilities, hospitals, nursing homes, healthcare providers, managed care organizations (MCOs), health maintenance organizations (HMOs), legal investigators relative to crimes and personal identification verification, coroners, school systems, travelers, motor vehicle operators, hazardous waste movements, tracking, and the like.

Patients and their healthcare providers would like to have a system that can be used to collect, store, maintain, and retrieve patient medical data in outpatient or inpatient settings. For example, approximately 97.1% of people in the United States are treated on an outpatient basis yet most patients do not have a medical record immediately at their disposal during these treatment episodes. That is to say, documentation is minimal, at best. When these patients are referred to other providers, clinics, HMOs, MCOs, and other healthcare facilities, they often take a hardcopy, portions of a hardcopy, or no medical record at all.

The healthcare industry needs a system that could dramatically improve outpatient care by creating an electronic medical record for each patient seen by outpatient providers; providing medical data to any authorized providers treating the same patient; by possibly reducing major illness and death due to drug contra-indication's; being an entry point for care management on an outpatient basis; allowing the provider treating the patient to send the patient's entire and current patient medical record to the aforementioned healthcare facilities; and allowing healthcare professionals to treat patients based upon concise, accurate, and current patient medical data for quick and accurate entry of treatment rendered into the patient's medical record at the time of treatment.

Moreover, there exists a need for a system that can be used to keep accurate records for: financial data, such as, credit cards, bank account data, deeds, birth certificates, etc; positive identification by using a digital photo; tracking school students' medical records, including immunizations, ADA requirements, and other conditions; tracking footprints of infants in case of emergencies, etc; tracking transportation and movement of hazardous materials; and accurately tracking and storing virtually any type of data.

Additionally, there is a need to ensure privacy and security for personal medical record information and the other aforementioned information. Access to these records should be secure and controlled by the owner of such sensitive records. In the case of medical records, these issues have garnered sufficient interest and strength to foster development of a number of broad rules for privacy and security under the Health Insurance Portability and Accountability Act (HIPAA) of 1996. Additionally, patients desire improved communication with their medical providers, mechanisms to reduce errors in their medical care, and better coordination of care among their various medical providers. A system that could address the aforementioned issues would be highly desirable.

Thus, a system and method for portable medical records solving the aforementioned problems is desired.

SUMMARY OF THE INVENTION

The system and method for portable medical records is capable of handling and updating portable medical records by consumers and by their health care providers. The system includes a portable electronic medical record having medical information about an individual stored in a fob-sized portable electronic device, such as a "memory stick". Data in the device is stored in reprogrammable non-volatile memory, such as FLASH memory having preferably a minimum of 2 GB capacity, and similar media.

The individual user and/or authorized healthcare providers may access the medical record information in the device via a standard USB port or other suitable external interface device. The system further may include an encryption system that provides user authorization for secure access to the electronic medical records by only those health providers/users having the required authorization. A simple password authorization may also be utilized.

The user can input information into the portable electronic medical record, as well as retrieve information that was input by users who are authorized healthcare providers.

An Internet web site can be provided for maintaining or updating the patient medical records for an existing user and/or for new users of the system, where each user can purchase his/her own portable electronic device and remotely upload his/her personal medical record into the device via a set of data entry forms securely presented to the user over the Internet. The only time that the Internet is needed is for new patients to create their own records or for existing patients to download or upgrade their records from remote locations out of the city when they have been lost. We will establish a data reduction center for creating patient records locally and updating these medical records. The patients have updated records in his/her possession, at every provider's office, at the clinics, hospitals, all other locations where the patient has been seen. Even a large hospital only needs a simple client server.

The system also allows for the healthcare professionals treating the patient to "only append" the permanent "read only" record by completing a pre-designed form that captures the data relative to that episode of treatment. Temporary storage of medical record information into a holding area in the electronic memory of the portable device is provided, pending authorization/authentication of a user, after which the holding area data can be transferred to the actual stored medical record, when time is permitting. In addition, the patient is required to request a completed hardcopy of the pre-designed form so that the patients' electronic medical record can be updated at a later date. These unique attributes insure that the patient's medical record is current. These data can be used by both the healthcare professionals and the patient in case of malpractice suits.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENT

The present invention relates to a system and method for portable medical records that provides a portable, electronic data storage device that is accessed and updated by authorized healthcare team members, specifically: consumers (patients), physicians, hospitals, ambulance personnel or EMTs, pharmacists, and the like. The device stores an individual's personal medical information, including demographics, contacts, physicians, insurance, employment, billing, diagnoses, surgeries, allergies, current and past medications, diet, vaccinations, preventive health measures, appointments, and reminders. In one embodiment, the portable electronic clinical medical record of the present invention can be resident in a memory stick, but a smart card or other portable memory storage device is also within the scope of the present invention.

According to the present invention, the patient is permitted to directly interact with and contribute to his/her own record. Additionally, the consumer, i.e., patient, can personally carry the record to physician offices and hospitals, and can grant permission for access to selected medical office and hospital personnel in order to enable those individuals to have direct access to the record(s) stored on the device. In this manner, the present invention provides healthcare providers with the capability of documenting each episode of care given to the patient, thus maintaining a current and accurate patient medical history that can be electronically transferred to other providers treating the same patient with the patient's consent.

Moreover, the present invention provides healthcare professionals with the capability of downloading patient care rendered by each provider to other authorized providers, clinics, HMOs, MCOs hospitals, and other authorized healthcare facilities directly from the PECMR directly into their computer, thus this present invention eliminates the requirement for using the Internet. These attributes eliminate the security risks of exposing patient data to unauthorized uses via the Internet. These attributes far exceed the security requirements for HIPAA compliance.

In addition, the present invention provides the catalyst for providing "patient care management" on an "outpatient" basis by allowing each healthcare professional treating the same patient to have a complete and accurate record of the patient's medical history, instead of patient medical data on the "human body parts" treated by our healthcare "specialists" today.

In addition, the present invention drastically reduces the pain and suffering of patients and possibly death of patients due to drug contra-indications (providers giving different medications to the same patient and not knowing what other medications are being giving by the other providers). It is estimated that about 120,000 patients die each year from drug contra-indications.

In addition, the present invention allows outpatient providers the capability to treat the same patient and exchange patient's medical data regardless of the organizational affiliation of the providers. Further, these attributes of this present invention can and should revolutionize America's philosophy for treating patients on an "outpatient" basis, where about 97% of patients are first seen.

Due to the aforementioned interface in combination with the portable electronic clinical medical record device (PECMR), the risk of Internet security problems is eliminated because personal medical records need not be retained online. Instead, the personal medical records can be retained by each person, at each outpatient healthcare professionals' offices, at each small and large medical clinic, at each hospital, and at any and all medical facilities where the patient has been or is being treated.

Figure 1:
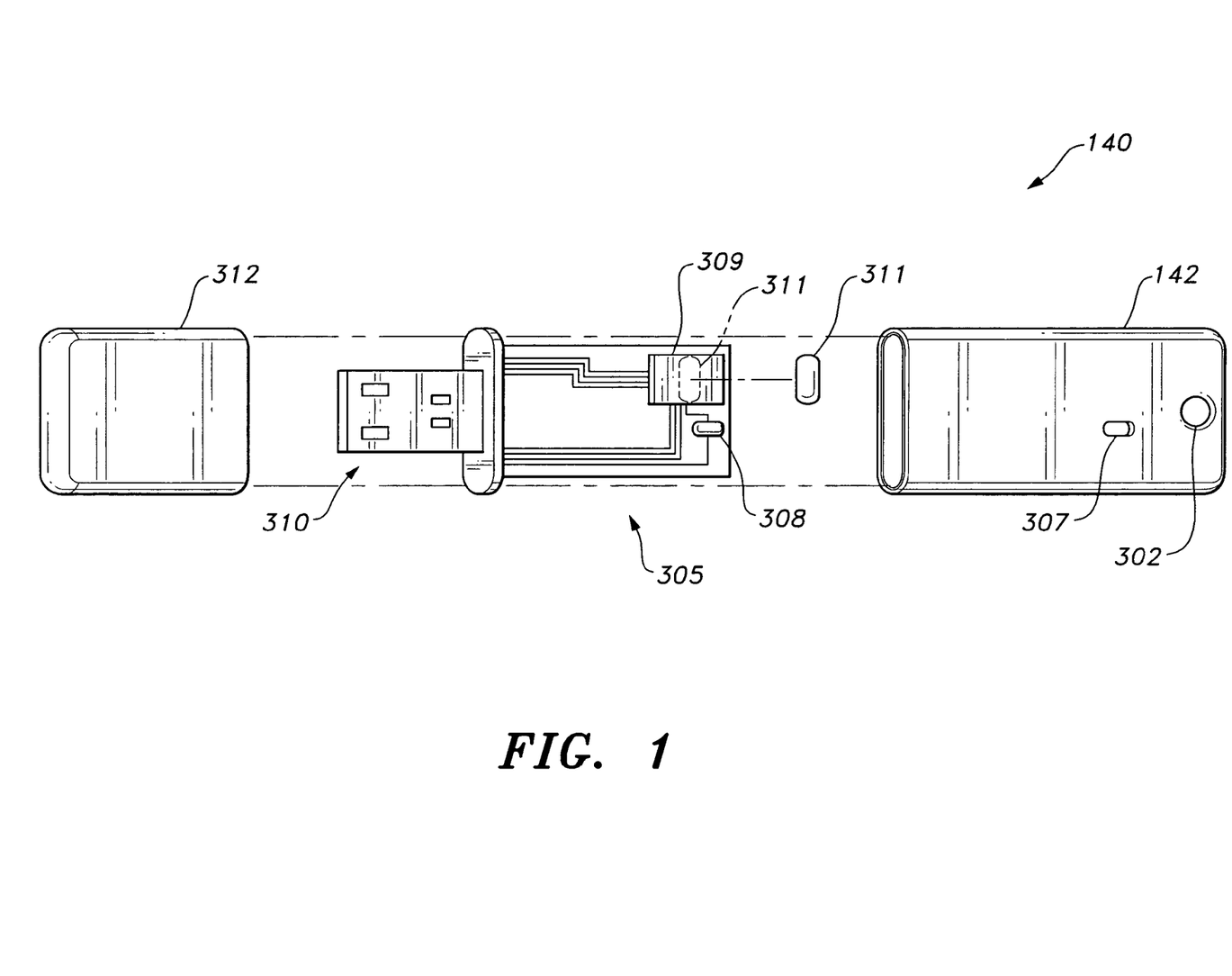
FIG. 1 is an environmental, perspective view of an electronic storage device in a system and method for portable medical records according to the present invention.
Figure 2:
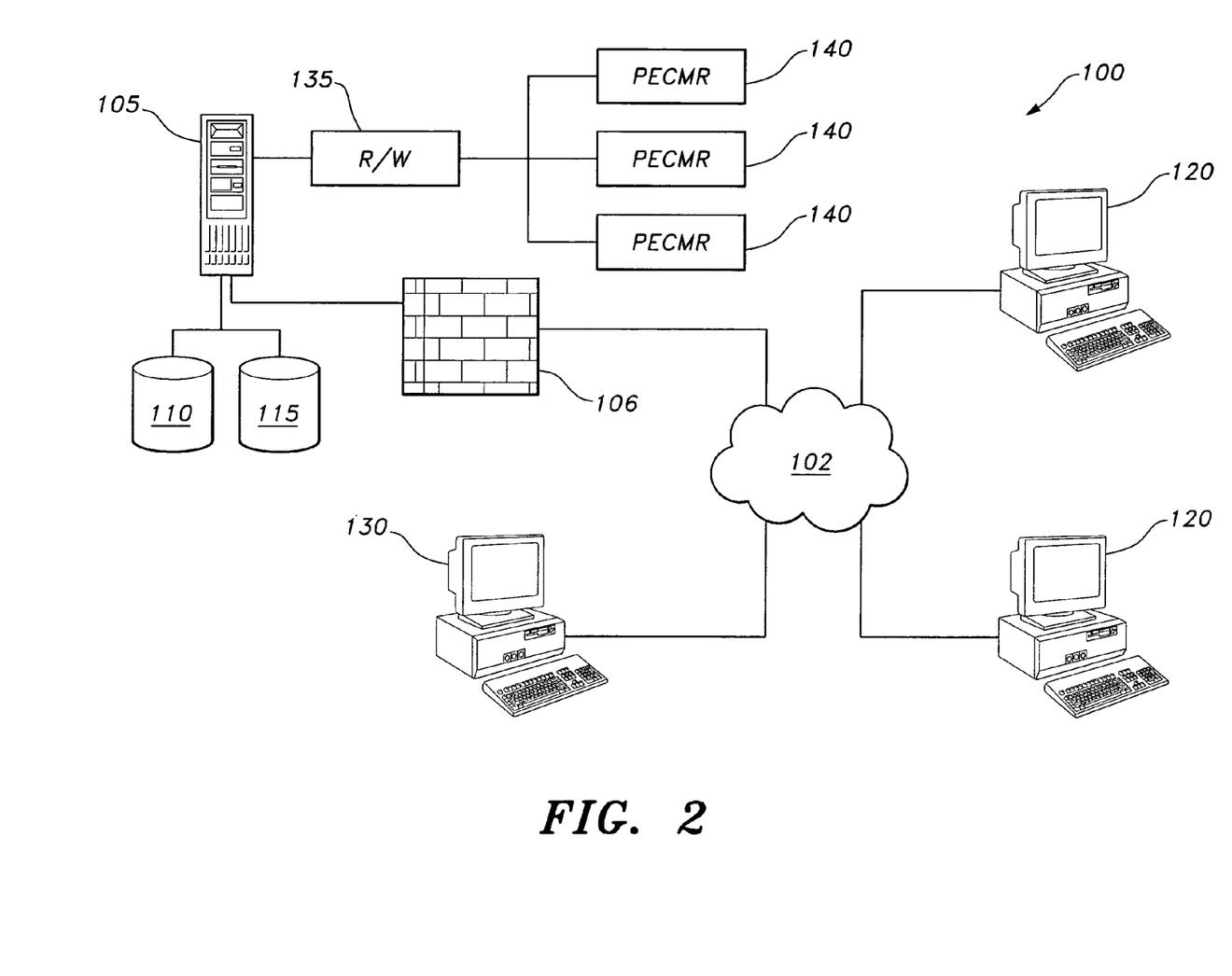
FIG. 2 is a block diagram of a system for portable medical records according to the present invention.

As shown in FIGS. 1 and 2, the PECMR device 140 comprises a memory device 305 having a USB plug 310 that can function as a bi-directional data port for the PECMR device 140. As noted above, the portable electronic clinical medical record (PECMR) can be stored in a memory chip, such as FLASH memory chip 309, USB FLASH drive, or any other suitable memory device that is reprogrammable, non-volatile and preferably has at least 1-gigabyte (GB) capacity. The memory chip 309 is encapsulated in a small fob sized housing 142, with the USB connector 310 extending from the housing 142. The USB connector 310 may be protected by a removable cap 312. An RFI/EMI shielding mesh 329 or similar shielding material may be disposed within the housing 142 and cap 312.

When stored in the aforementioned manner, the PECMR provides a digitized integrated patient medical record database that contains accurate, concise, and current patient data, including comprehensive patient history data necessary for healthcare professionals to provide required medical treatment in a professional, cost-effective, and timely manner. Device 140 has the capability of storing any digitized medical information, including, but not limited to, photos, footprints, fingerprints, radiological images (x-rays, CT scans, and the like), teeth images, prescriptions, etc. Additionally, demographic (name, address, next-of-kin, telephone numbers, e-mail, emergency notification, religion preference, insurance carriers, relationships (such as sponsor, contact, relatives, etc.), allergy/asthma information, disease information (e.g., Diabetes, Cardiovascular diseases, and the like), specific information related to organs (such as eyes, heart, kidneys, feet, skin, nerves, and the teeth/mouth), cancer, respiratory, OB/GYN information, Radiology, Pharmacy (for a list of medications and prescriptions), laboratory, hospitalization (surgery), and many other types of medical data may be stored in the PECMR.

Figure 4:
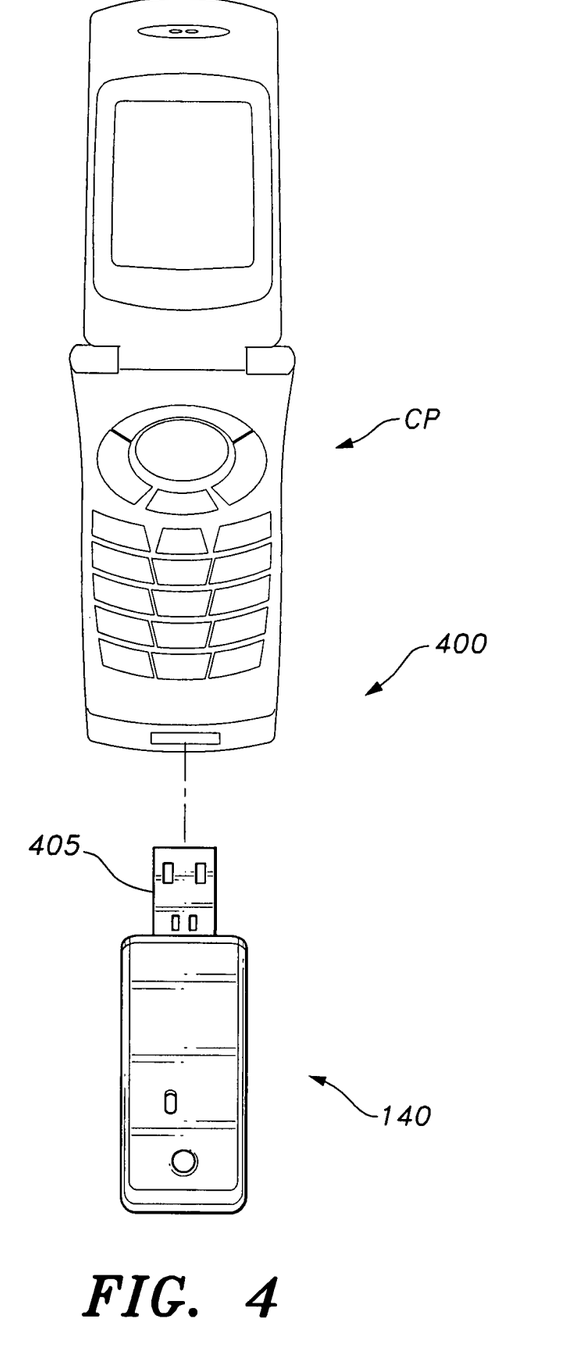
FIG. 4 shows a cell phone-ready embodiment of an electronic storage device in a system and method for portable medical records according to the present invention.
Figure 5:
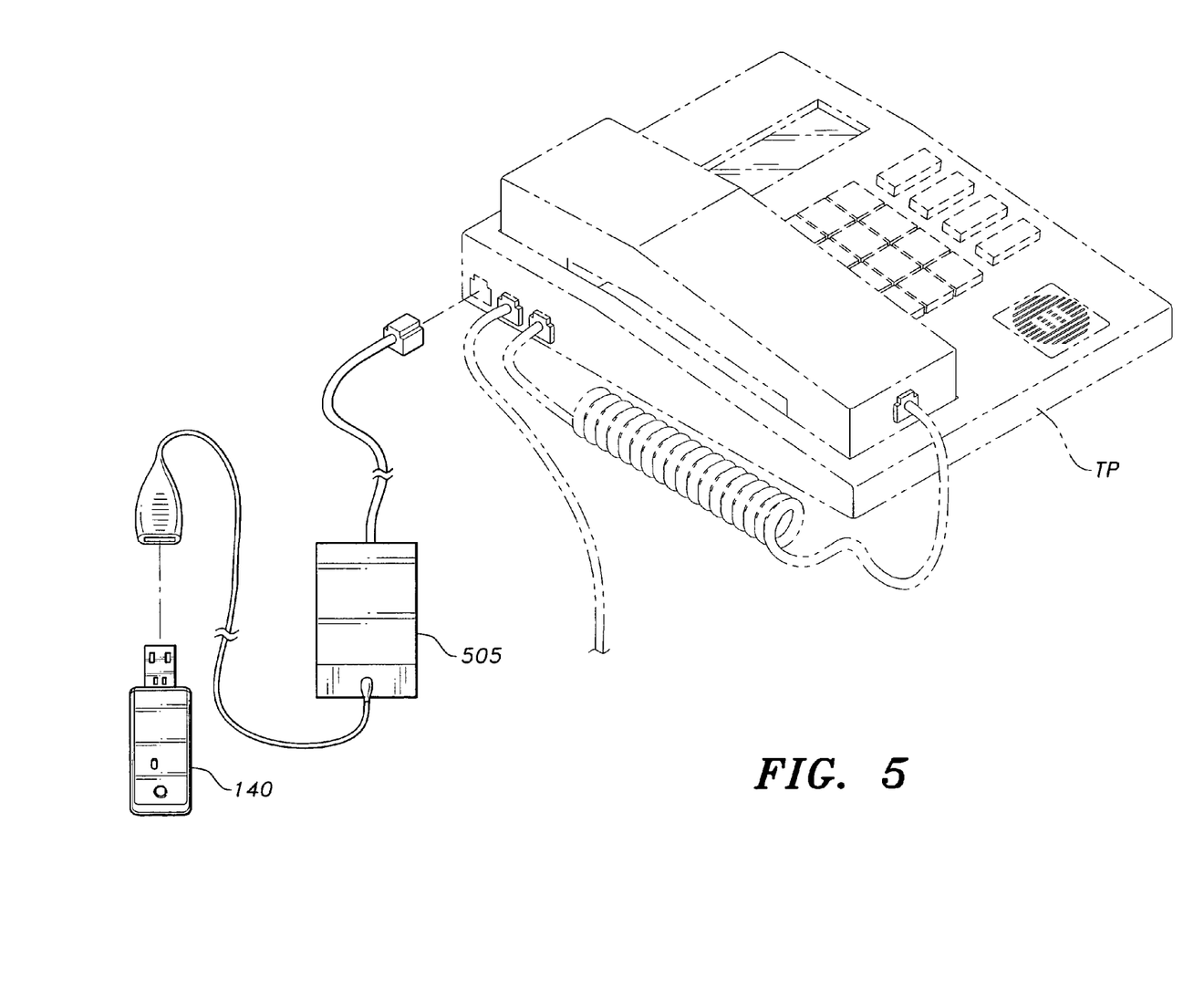
FIG. 5 is a partially exploded perspective view of the portable medical records device and adapter cord for telephone according to the present invention.
Figure 6:
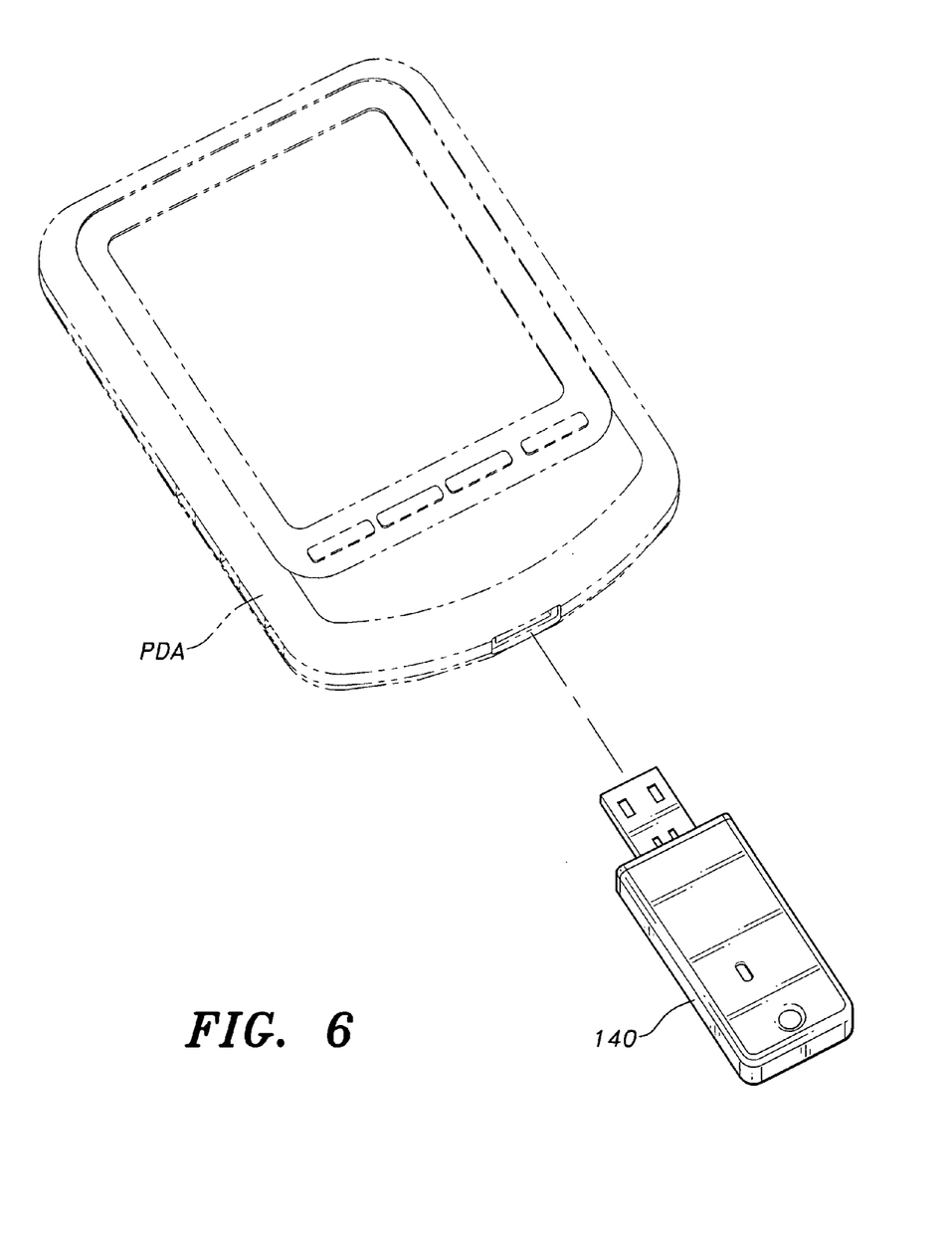
FIG. 6 is a perspective view of the portable medical records device and a PDA according to the present invention.

Instead of medical records, the memory device 309 could alternatively be loaded with financial data (credit card, bank accounts, etc), administrative data (deeds, property insurance data, etc) and other data such as, hazardous materials tracking, transportation data (trucks, large vehicles monitored by the Department Of Transportation (DOT)), and the like. It is also within the scope of the present invention to include an interface capable of operable data communication via standard telephone, portable radio, cell phone, and the like. For example, as shown in FIG. 4, a system 400 may comprise a PECMR device 140 that can send and receive data via cell phone CP when connected via phone compatible connector 405. As shown in FIG. 5, a PECMR device 140 can, via adapter 505, be connected to a standard telephone TP for dial-up data communication. As shown in FIG. 6, the PECMR device 140 can be connected via compatible connector to a PDA. Moreover, software management of the portable medical records database 115 may be performed on the PDA so that a health care professional can store medical records of entire families or an entire medical practice clientele on his/her PDA.

For security purposes, a dye-pack capsule 311 filled with water or some combination of corrosive fluid or gel capable of rendering the portable electronic device 140 inoperable upon physical tampering is disposed within the housing 142 proximate the chip 309 or other suitable area of the memory stick 305. When the device 140 is tampered with, the capsule 311 breaks, discharging its contents within housing 142 and onto the memory stick 305, permanently damaging chip 309 so that its contents cannot be retrieved.

When the device 140 is in use, an indicator light 308, being disposed within the device on the circuit board of the memory stick 305, becomes active to indicate operations, such as transfer and overwriting of information via the interface with a computer, e.g., server 105 or computers 120, using an appropriate interface, such as USB Read Write (R/W) interface 135. The housing 142 has a viewport 307 so that the status light 308 is visible when illuminated. Status light 308 may function as an operations indicator light to indicate that the database and database management software and all system components are operational and functioning properly.

A throughbore 302 capable of functioning as a key chain hole is disposed at one end of the housing 142 of the PECMR device 140 in order to provide the user with a convenient means of transport on his/her person at all times with a lanyard, key chain, or the like.

Figure 3A:
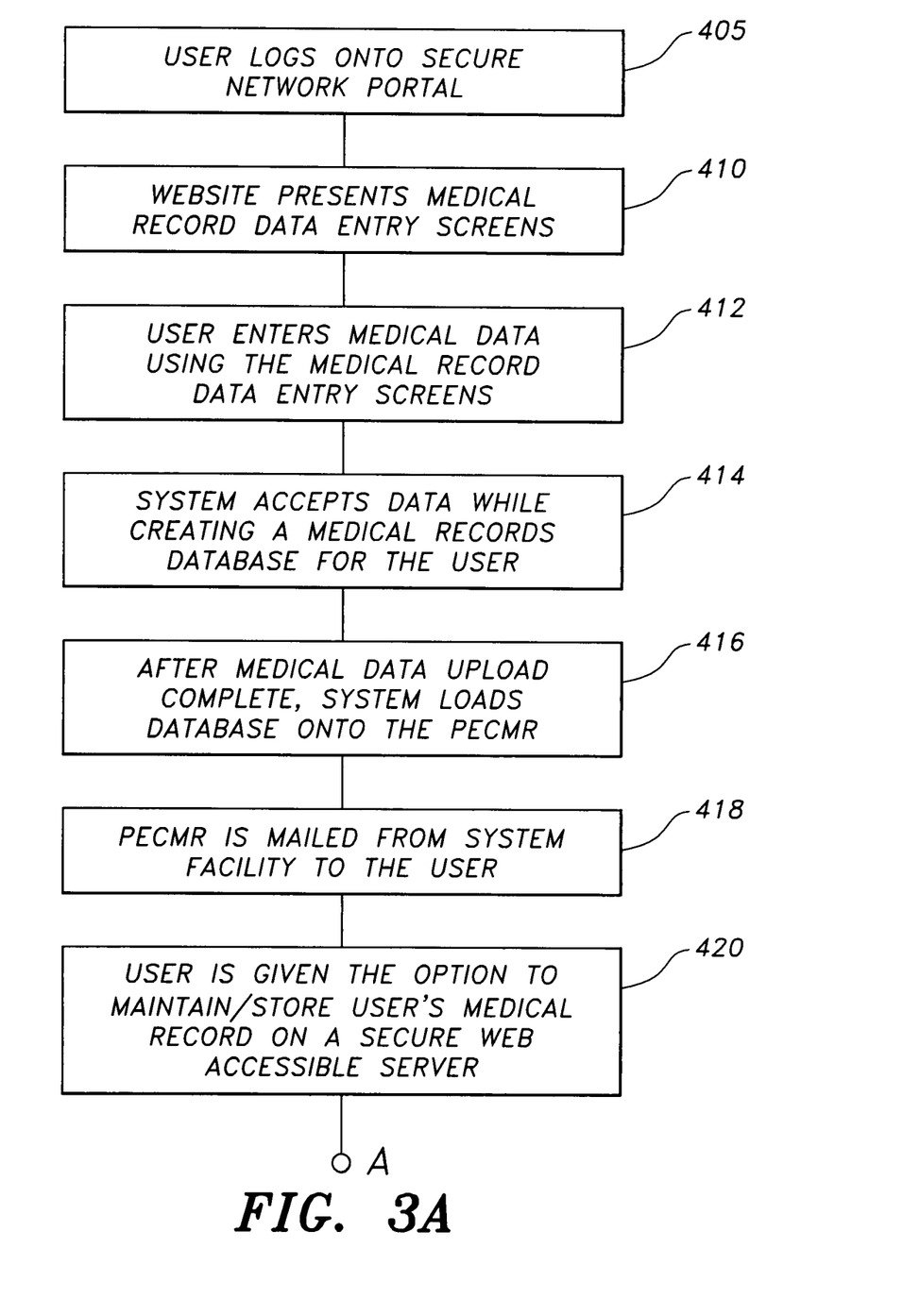
FIGS. 3A, 3B and 3C represent a flowchart of a method for portable medical records according to the present invention.
Figure 3B:
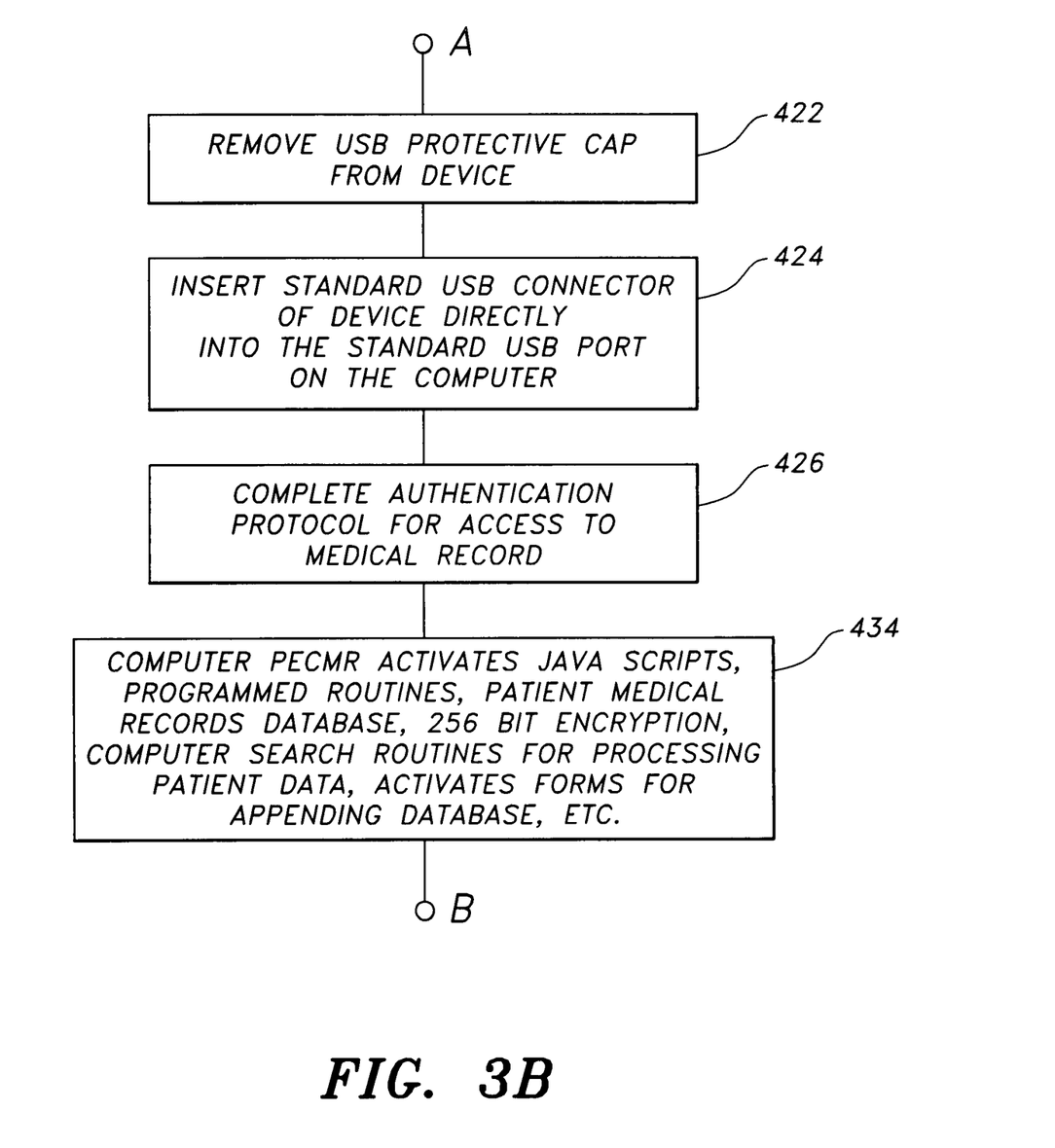
Figure 3C:
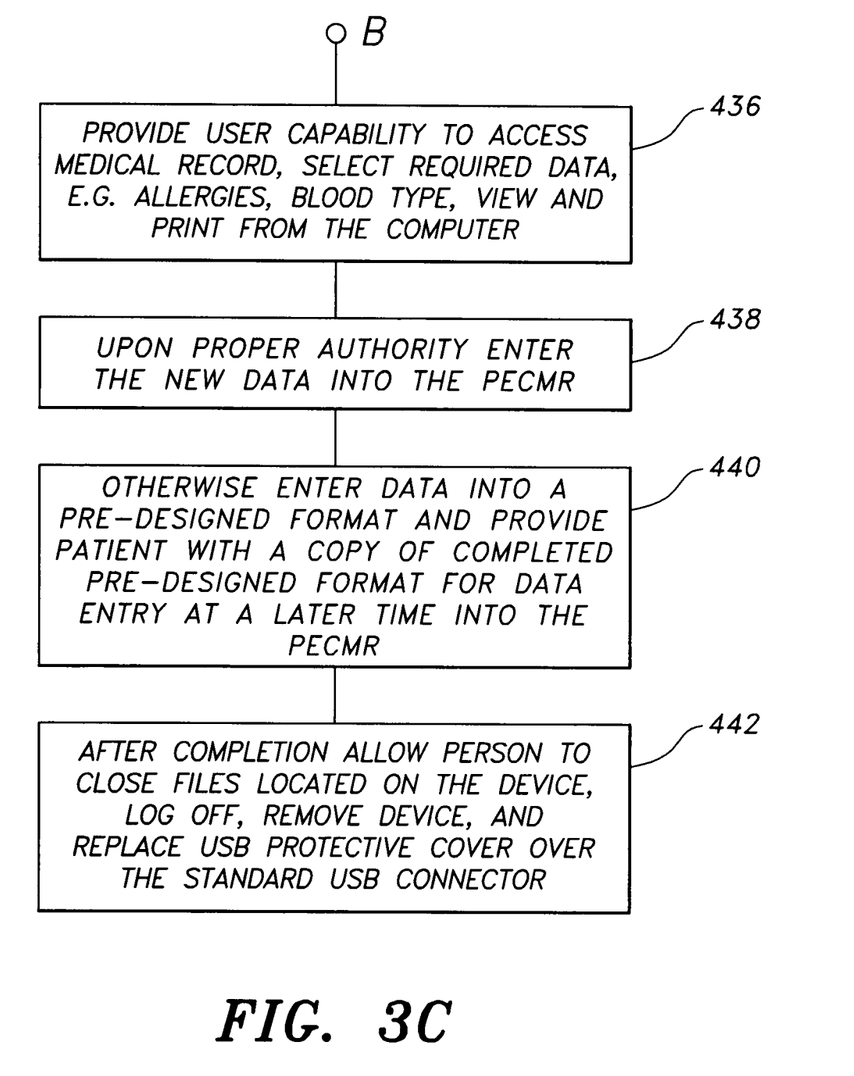

As shown in FIG. 2, a Back Office infrastructure 100 having Internet 102 capability is provided to initialize and distribute the PECMR device 140 to a user who has purchased or leased the device 140. Users having an Internet-ready Web-enabled device, such as computers 120, a PDA, a laptop, a notebook, a cell phone, and the like, may log onto a secure web site provided by server 105. Firewall 106 provides data security in the processing of personal medical records by system components, such as server 105. Web pages and forms data required by users to complete their medical records may be stored in mass storage database, such as forms database 110. FIGS. 3A-3C show a method of the invention that does not need to be online to the Internet. FIGS. 3A-3C outline the method for maintaining medical records of existing users and for new users desiring to create their electronic portable medical record from a remote location. The Internet is not required to provide the patient's medical record needed for treating the patient. All of the patient's medical records data are contained on the PECMR 140.

Additionally, the medical records data used by the server 105 in creating portable electronic clinical medical records may be permanently or temporarily stored in records database 115. It should be understood that health care providers may also log onto the system 100, provided that the health care providers have computing equipment, such as workstation 130, a PDA, a laptop, a cell phone, or the like, and may create medical records on behalf of their patients. Server 105 and associated data storage devices are capable of maintaining all patient medical data records input into the system 100. Users may also be provided with the option to create the patient database, i.e., PECMR, without the use of the Internet.

As shown in FIGS. 3A-3C, the method allows the user or healthcare provider to log onto a secure network portal 405. A web site presents medical records data entry screen 410. As shown at step 412, the user can enter medical data using the medical record data entry screens. At step 414, the system 100 accepts the data while creating a medical records database 115 for the user. The medical records database 115 provides a baseline of the user's (patient's) health status and functions as a useful tool for research. The baseline data resides in the medical records database 115 and is comprised of a baseline date associated with patient baseline health status information. This baseline data is write-once and thereafter read only without special permissions.

Using the medical records database 115, the service provider may track patient progress, track effects of medications, and compare treatment episodes to determine treatment efficacy and the like. The system prohibits the baseline data from being downloaded into another computer or electronic media. However, after treatment has been rendered by the healthcare provider, the software prompts the healthcare provider to complete an electronic form attached to the original patient record allowing healthcare providers to document the current treatment rendered prior to exiting the device 140. This insures that the patient's medical record is updated at the time of treatment.

However, if the healthcare provider elects not to update the portable medical record at the time of treatment, the patient can request a hardcopy and update the medical record at a later time. Updates to the medical record in this manner provides a documented audit trail of all treatments rendered to the patient and may be vital to protect both the patient and the provider in case of potential malpractice claims.

Additionally, the medical records database 115 is designed to be compatible across a variety of service providers and platforms. The patient's medical records data can be stored at each medical facility on a single server and does not need to interface with any other outside source or computer. At step 416, after the medical data upload to the server 105 is completed, the user's medical record database is loaded onto the PECMR device 140 via interface 135. As shown at step 418, the facility can then mail, or otherwise distribute, the PECMR device 140 to the user. As shown at step 420, the user is given the option to maintain and/or store his/her medical record on the server 105. The portable medical records database 115 is based upon primary data elements known in the art, such as data elements of the Veterans Administration Computerized Patient Records System (CPRS). However, the medical records database 115 preferably has a data structure that avoids the necessity of containing cumbersome Admissions, Discharge, and Transfer (ADT) data, and the like. The data of PECMR device 140 may carry a standardized format of data written in JAVA (free software) that can be read by any computer, cell phone, PDA, and telephone via device interfaces.

As shown in FIG. 3B, when the user/healthcare provider is ready to utilize the PECMR device 140, he/she removes the USB protective cap 312 from the device (step 422). Subsequently, at step 424, the PECMR device 140 is activated by insertion of the standard USB connector 310 directly into a standard USB port on the computer, e.g. 120 or 130. At step 426, an authentication protocol is completed, and upon success the portable electronic clinical medical record is made accessible to the user.

At step 434, any required scripts, computer software, and the medical records database are automatically activated within the PECMR device 140. The software includes electronic medical record management software that is preferably uploaded along with the electronic medical record. The electronic medical record management software provides processing capability of reading, writing, modifying, and re-saving PECMR records in the portable memory device 140.

The electronic medical records management software may be written in JAVA or any other suitable programming or scripting language. Status indicator light 308 on memory device 140 may illuminate or blink to indicate the status of the load operations. As shown in FIG. 3C at step 436, the user is provided with the capability to access the portable medical record, select required data (such as allergies, blood type, and the like), and then view and print from the computer 120 or 130.

At step 438, upon proper authentication, new data may be entered into the portable electronic clinical medical record. As shown at step 440, unauthenticated data may be stored in a reserved holding area within the PECMR. Thus, a record of a treatment episode can be entered into the reserved location, but does not get recorded into the permanent medical record until the reserved location data is authenticated by an authorized healthcare provider having required access codes to "modify and/or update" the patient's medical records database. At step 442, when data operations are completed the user is allowed to close files located on the device, log off and remove the device and then replace the USB protective cover back onto the unit 140. To provide additional security, the PECMR management software removes itself and the PECMR from the computer 120 or 130, not only from the header or FAT tables of the disk, but also by overwriting the data sectors of the disk that were used for temporary storage of the data.

Preferably, a key management system is provided, and includes an encryption system, such as, for example, Rivest, Shamir Adleman (RSA), Pretty Good Privacy (PGP), and the like, capable of providing user authorization for secure access to allow a health care provider access to the patient's portable electronic clinical medical record so that it can be electronically read and/or updated by the health care provider. The patient database can be secured from unauthorized access via secured LOGON and PASSWORD up to and exceeding 128-bit encryption. The use of 256-bit encryption is preferable.

PECMR database for each patient's medical record is "self-sustained" on the portable device 140 and contains all medical record data elements and can exceed HIPAA privacy and confidentiality codes for accessing medical data, storing medical data, processing medical data, and transmission of medical data. For example, the present invention can provide medical information in Electronic Data Interchange (EDI) format in accordance with HIPAA, MEDICARE, and MEDICAID requirements. Patient medical records data may have a predetermined number of security levels each having unique access protocols. Exemplary security levels are summarized below.

Security Level 1—Emergency Medical Data, including: Digital Photo of each patient; Demographic Data; Emergency Notifications (Providers, Next-of-kind, etc.); Allergies and Immunizations; Vital Measurements; Blood Type; Medications (History, Current, Inactive); Laboratory Data; Pharmaceutical Data (Prescriptions); Radiological Data (Data about X-Rays, CATSCAN, Images, etc); Optometry Data (Prescriptions for glasses, test results, etc.); Surgery Data (Operations, dates, providers, facilities, etc.); Special and additional data for Diabetics; Immunizations (School children-critical); Cardiology, urology, nephrology, dermatology, podiatry, etc.; Anesthesiology; Colon and Rectal Surgery; Dermatology; Emergency Medicine; Family Medicine; Internal Medicine; Neurology; Nuclear Medicine; Opthalmology; Orthopedic Surgery; Otolaryngology; Pathology; Pediatrics; Physical Medicine and Rehabilitation; Preventive Medicine; Psychiatry; Radiation Oncology; and Thoracic Surgery.

Security Level 2—Critical Diseases includes HIV/AIDS and Others.

Security Level 3—Financial Data includes Credit cards; Banking data; Deeds; Birth Certificates; Wills; and Copy of Driver's Licenses.

Emergency healthcare professionals, such as EMTs or the like, may have open access (no password required) to a predetermined subset of the Security Level 1 data. For example, the first seven Security Level 1 elements listed above may be openly accessible to the emergency healthcare professionals.

Additionally, the present invention provides records synchronization, i.e., the automatic storage of an access file in the provider's computer database, which is synchronized with the consumer's PECMR portable record each time the record is accessed. When patients return home from a provider visit, they can view and/or print an access file directly from their portable record that details the names of all users who have accessed their personal health information, the date and time of each access, and an indication of whether a reading or writing event occurred. When patients return again to their medical providers, use of the portable electronic medical record automatically updates the access file of the device 140 to include any access events that have occurred in the provider's computer database since the prior office visit. Patients therefore automatically obtain a complete file detailing all episodes during which their personal health information was accessed both during their provider visits and between their provider visits.

In summary, the system and method for portable medical records provides a system and method wherein the record can be updated by users (including authorized health care providers) to permit integration with the electronic medical records used and updated by healthcare providers both in medical office and hospital settings. Use of the present invention results in better "managed care" and/or outpatient care management outcomes wherein healthcare providers specializing in the various biological systems of the patient can be aware of each other's treatment regime and communicate with each other to provide a holistic approach to treatment of diseases such as diabetes, and the like. Using the PECMR device 140 outpatient healthcare providers, and others seeing the same patient can exchange patient medical data among themselves, thus providing more comprehensive, timely, and cost-effective healthcare to each patient, thereby reducing major illness and death due to drug contra-indications. The net effect is the avoidance of redundant services, the avoidance of medical errors, and a significant improvement in the quality of healthcare.

The system and method provides for secure transfer of health information between the portable electronic health record, the patient, the providers, the hospitals and other healthcare facilities by directly entering the PECMR into a computer with a USB port at any location. Unlike most of the systems in America today, this' present invention does' not need the Internet to transfer health information, to transfer patient information; nor does it need the Internet to transfer patient data necessary to treat the patient. All medical treatment data, computer programs, computer routines, encryption, patient database, security, etc. can be self-contained in the PECMR 140 and carried in the possession of the patient on the portable device 140. Unlike many systems that use the Internet to transfer health information, the link to the portable electronic medical record may be a direct and dedicated one wherein the record is read using a provider's computer 130 or other access device.

As discussed above, the system provides a patient with the capability of printing out medical record information in the portable electronic health record via a printer (not shown) so that the patient can physically take the printed information to the health care provider.

It is within contemplation of the present invention that any number or type of health care providers can utilize the system. Clinics, hospitals, dentists, specialists, and the like, may all utilize the system and method.

It is to be understood that the present invention is not limited to the embodiment described above, but encompasses any and all embodiments within the scope of the following claims.

I claim:

1. A portable individual user-carried system for portable individual medical records, comprising:

a computer that reads, writes and modifies information in an electronic medical record;

a real time prompt that updates the treatment of the individual user at the time of the treatment;

an external device interface wherein the individual inputs information into the electronic medical record;

a portable electronic device carried and accessible solely by the individual user, the portable electronic device consisting of:

a fob-sized housing; the fob-sized housing containing a computer readable memory, wherein the individual user's medical records are stored in the computer readable memory;

a bi-directional data port that communicates with the external device interface of the computer once connected to the computer;

a Radio Frequency Interference/Electromagnetic Interference shield disposed within the fob-sized housing;

a dye-pack capsule disposed within fob-sized housing, wherein the dye-pack capsule renders the portable electronic device inoperable upon physical tampering is disposed within the housing proximate of the chip or other suitable area of the readable memory;

instructions stored on a medium when executed by the computer causes the computer to perform the steps of:

determining that the bi-directional data port of the portable electronic device is in communication with the external device interface of the computer;

based on a determination that the bi-directional data port of the portable electronic device is in communication with the external device interface of the computer, receiving by the portable electronic device the electronic medical record from the computer;

storing by the portable electronic device the received electronic medical record from the computer within the computer readable memory;

creating a medical record that comprises a first field and a second field;

a) the first field stores digitized medical information, wherein the first field includes first, second, and third security levels, each of the security levels having unique security access protocols; wherein the first security level includes medical record data selected from the group consisting of emergency medical data, identification data, demographic data, emergency notification data, allergy data, immunization data, vital measurement data, blood type data, medication data, laboratory data, radiological data, optometry data, surgical data, condition-specific data, body part-specific data, and combinations thereof; wherein the second security level including medical record data related to critical diseases; and wherein the third security level including data selected from the group consisting of financial data, birth certificate data, last will and testament data, driver's license data, and combinations thereof;

b) the second field stores data, wherein the data includes an interactive web-page to the user, the interactive web-pages having forms for creating, editing, and updating the electronic medical record, further wherein the second field generates a secure means that password protects access to the stored digitized medical information in the created second field; and an encryption system that provides user authorization for secure access via the bi-directional port to the medical information stored in the portable electronic device.

2. The system for portable medical records according to claim 1, wherein the computer readable memory in the portable electronic device comprises electronic FLASH memory having at least one gigabyte capacity.

3. The system for portable medical records according to claim 1, wherein the portable electronic device sends and receives data by a communications device selected from the group consisting of a cell phone, a personal digital assistant, and a landline telephone.

4. The system for portable medical records according to claim 1, further comprising a dial-up modem adapter and a telephone connected to the modem adapter, the modem adapter being connected to the portable electronic device.

5. The system for portable medical records according to claim 1, further comprising a personal digital assistant having portable medical records database management software resident thereon.

* * * * *